US008880187B2

(12) United States Patent
McDonald et al.

(10) Patent No.: US 8,880,187 B2
(45) Date of Patent: Nov. 4, 2014

(54) NEUROSTIMULATION LEAD DESIGN WITH VARYING RF IMPEDANCE FILARS

(71) Applicant: Boston Scientific Neuromodulation Corporation, Valencia, CA (US)

(72) Inventors: Matthew Lee McDonald, Pasadena, CA (US); Gaurav Gupta, Valencia, CA (US); Jacob Matthew Muhleman, Canandaigua, NY (US); Ross Daniel Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/801,608

(22) Filed: Mar. 13, 2013

(65) Prior Publication Data

US 2013/0245734 A1    Sep. 19, 2013

Related U.S. Application Data

(60) Provisional application No. 61/612,100, filed on Mar. 16, 2012.

(51) Int. Cl.
*A61N 1/05* (2006.01)
*A61N 1/08* (2006.01)

(52) U.S. Cl.
CPC .. *A61N 1/08* (2013.01); *A61N 1/05* (2013.01); *A61N 2001/086* (2013.01)
USPC ........................................................ 607/116

(58) Field of Classification Search
CPC ... A61N 1/05; A61N 1/056; A61N 2001/086; A61N 1/0563; A61N 1/08; A61B 5/042; A61B 18/1233; A61B 2562/0209

USPC .................................................. 607/115–122
See application file for complete search history.

(56) References Cited

U.S. PATENT DOCUMENTS

| | | | |
|---|---|---|---|
| 5,935,159 A * | 8/1999 | Cross et al. | 607/116 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,239,923 B1 * | 7/2007 | Tockman et al. | 607/119 |
| 7,244,150 B1 | 7/2007 | Brase et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,335,570 B2 | 12/2012 | McDonald | |
| 8,364,278 B2 | 1/2013 | Pianca et al. | |
| 8,364,279 B2 | 1/2013 | McDonald et al. | |

(Continued)

*Primary Examiner* — Rex R Holmes
(74) *Attorney, Agent, or Firm* — Lowe Graham Jones PLLC; Bruce E. Black

(57) ABSTRACT

An implantable stimulation lead includes a lead body having a proximal end and a distal end; a plurality of electrodes disposed along the distal end of the lead body; a plurality of terminals disposed along the proximal end of the lead body, and a plurality of conductors disposed in the lead body and including a first conductor and a second conductor. Each conductor electrically couples at least one of the electrodes to at least one of the terminals. The first conductor has a RF impedance that is at least 25% greater in magnitude than the second conductor.

19 Claims, 4 Drawing Sheets

(56) References Cited

U.S. PATENT DOCUMENTS

| | | |
|---|---|---|
| 8,380,324 B2 | 2/2013 | McDonald et al. |
| 2007/0150036 A1 | 6/2007 | Anderson |
| 2008/0243218 A1 | 10/2008 | Bottomley et al. |
| 2008/0262584 A1 | 10/2008 | Bottomley et al. |
| 2010/0256693 A1 | 10/2010 | McDonald et al. |
| 2011/0046706 A1 | 2/2011 | McDonald et al. |
| 2011/0230893 A1 | 9/2011 | Barker |
| 2012/0019116 A1 | 1/2012 | Fan |
| 2012/0029596 A1 | 2/2012 | Barker |
| 2012/0071937 A1 | 3/2012 | Sundaramurthy et al. |
| 2012/0158072 A1 | 6/2012 | Venook et al. |

* cited by examiner

NEUROSTIMULATION LEAD DESIGN WITH VARYING RF IMPEDANCE FILARS

CROSS-REFERENCE TO RELATED APPLICATIONS

This application claims the benefit under 35 U.S.C. §119 (e) of U.S. Provisional Patent Application Ser. No. 61/612,100 filed on Mar. 16, 2012, which is incorporated herein by reference.

FIELD OF THE INVENTION

The present invention is directed to the area of implantable electrical stimulation system and methods of making and using the system. The present invention is also directed to implantable electrical stimulation system having conductive wires with different RF impedances and methods of making and using the system.

BACKGROUND

Implantable electrical stimulation has proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to the body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

When patients implanted with, or example, deep brain stimulation (DBS) or cardiac pacing (CP) lead systems are exposed to external Radio Frequency (RF) fields, local tissue damage around the electrodes of these leads can occur. During an MRI scan, the transmit RF field generates current along the conductors within an implanted lead. The current is then delivered through the conductors and into the surrounding tissue. Where the current emerges from the electrodes coupled to the conductors, it can be concentrated and can cause heating and subsequent tissue damage.

BRIEF SUMMARY

One embodiment is an implantable stimulation lead including a lead body having a proximal end and a distal end; a plurality of electrodes disposed along the distal end of the lead body; a plurality of terminals disposed along the proximal end of the lead body, and a plurality of conductors disposed in the lead body and including a first conductor and a second conductor. Each conductor electrically couples at least one of the electrodes to at least one of the terminals. The first conductor has a RF impedance that is at least 25% greater in magnitude than the second conductor.

Another embodiment is a method for tissue stimulation that includes implanting the implantable stimulation lead described above within a body; and providing electrical stimulation signals to the electrodes of the implantable stimulation lead to stimulate adjacent tissue.

Yet another embodiment is an implantable stimulation system that includes a control module for producing electrical pulses; and the implantable stimulation lead, described above, coupleable to the control module.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DESCRIPTION OF THE EMBODIMENTS

Figure 1:
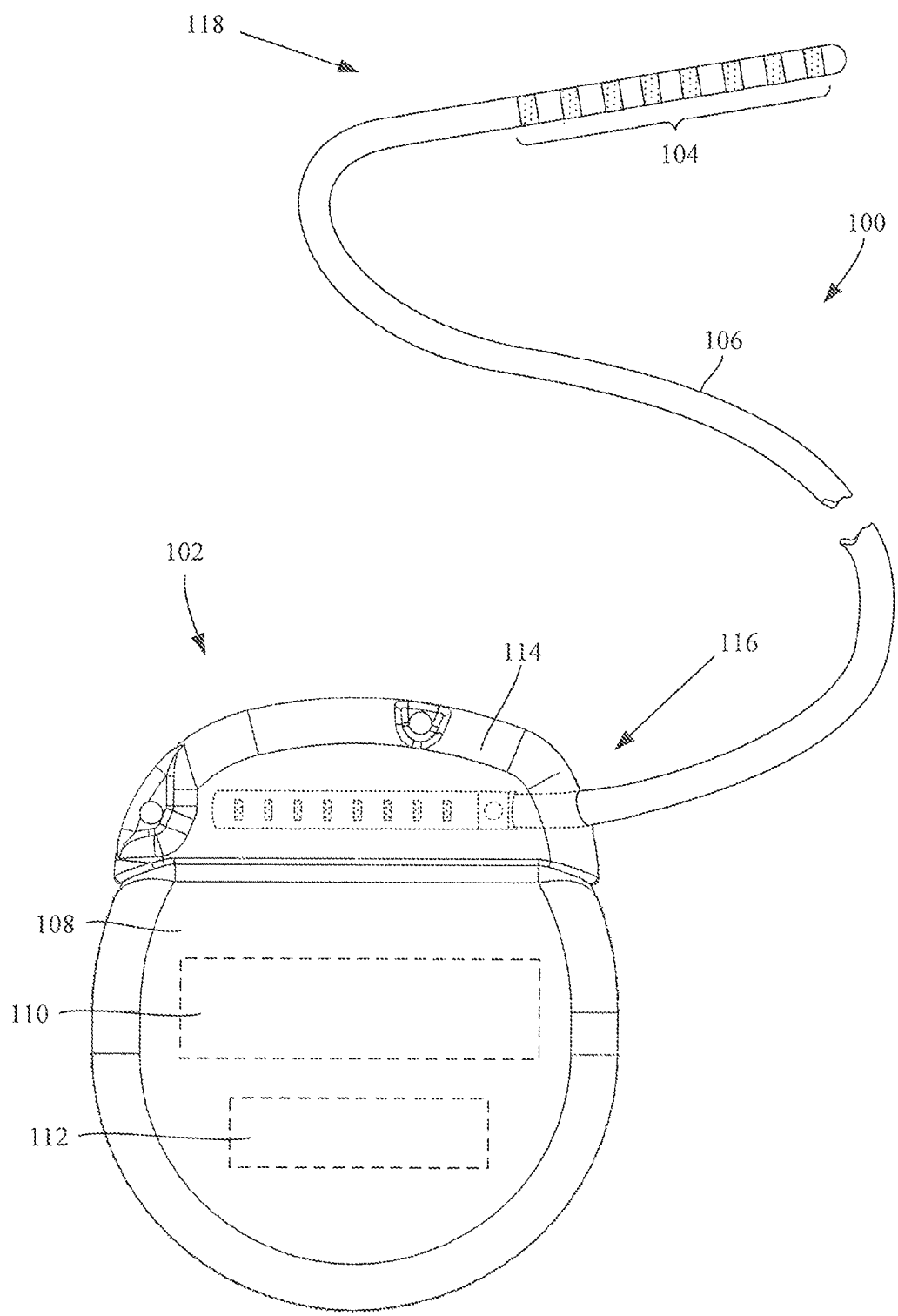
FIG. 1 is a schematic side view of one embodiment of an implantable stimulation system, according to the invention.

The present invention is directed to the area of implantable electrical stimulation system and methods of making and using the system. The present invention is also directed to implantable electrical stimulation system having conductors with different RF impedances and methods of making and using the system.

The term "high radiofrequency" or "high RF" refers to RF frequencies that are at or above 1 MHz, and includes frequencies in the range of, for example, 1 MHz to 256 MHz. For example, for 1.5 T, 3.0 T and 6.0 T MRI systems, the respective MRI RF frequencies are 64 MHz, 128 MHz and 256 MHz.

The term "coiled" refers to a conductive lead (conductor, trace, wire or filar) that has a coiled configuration. The term "co-wound" means that the affected leads, conductors, wires or filars can be substantially concentrically coiled at different diameters, one above the other, or concentrically coiled, preferably closely spaced, at substantially the same diameter. The term "co-wound" is used to describe a structure and is not limiting to how the structure is formed (i.e., the coiled segments are not required to be wound concurrently or together, but may be so formed). The terms "conductive element" and "conductors" are used interchangeably and refer to a conductive path that connects target components (such as, for example, a stimulation source and an electrode) and can include one or combinations of a metallic trace, a wire, a flex circuit, a filar, or other conductive configuration. As such, the conductors or conductive elements include long linear and/or non-linear conductors that can be formed with one or more of discrete wires, flex circuits, filars, or by plating, etching, deposition, or other fabrication methods for forming conductive electrical paths.

Suitable implantable electrical stimulation systems include, but are not limited to, a lead with one or more electrodes disposed on a distal end of the lead and one or more terminals disposed on one or more proximal ends of the lead. Leads include, for example, percutaneous leads, paddle leads, and cuff leads. The implantable stimulation systems also typically include a control module, which is often implantable, such as an implantable pulse generator (IPG). Examples of implantable stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and 8,364,278; and U.S. Patent Application Publication Nos. 2007/0150036; 2011/0230893; 2012/0029596; 2012/0071937; and 2012/0191167, all of which are incorporated by reference. Electrodes at the distal end of the leads are coupled to the terminals at the proximal end by conductors.

Patients with an implanted electrical stimulation system may undergo magnetic resonance imaging ("MRI") procedures. Conventional electrical stimulation systems may be potentially unsafe for use with MRI due to the effects of electromagnetic fields in an MRI environment. A common mechanism for causing the electrical interactions between the electrical stimulation system and RF irradiation is common-mode coupling of the applied electromagnetic fields that can act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits of the electrical stimulation system, such as circuits within the control module.

Some of the effects of RF irradiation may include, for example, inducing current in the lead, causing undesired heating of the lead that may potentially cause tissue damage, undesired or unexpected operation of electronic components, or damage to (including premature failure of) electronic components of the implantable stimulation system (e.g., electronic components in the control module). Additionally, when an electrical stimulation system is used within an MRI scanner environment, the electrical interactions between the electrical stimulation system and the MRI may cause distortions in images formed by the MRI system.

In some cases, the cumulative amount of RF energy propagating from the lead to the electronic subassembly may be tolerable to the tissue surrounding the lead electrodes and to the electronic components in the control module. However, when the RF energy is more unevenly distributed among the lead conductors, the lead terminals and electrodes having relatively-high concentrations of RF energy may develop one or more undesirable RF "hot spots" having concentrations of RF energy that are significantly higher than RF energy concentrations at other lead electrodes and terminals. In some cases, one or more of the "hot spots" may have RF energy concentrations that are high enough to cause tissue damage or damage to electronic circuits within the control module. Accordingly, it may be desirable to distribute RF energy propagating along the different leads conductors more uniformly to prevent RF "hot spots" from developing.

An MRI-safe electrical stimulation system has been identified as one of the main features desirable for new implantable stimulation systems. An electrical stimulation system can provide more uniform distribution of RF energy to each lead terminal. To this end, leads can be provided with differing RF impedance between the different conductors.

In the following, embodiments will be described with reference to deep brain stimulation. It is understood that this choice is merely exemplary, and that the device may be utilized in other systems, and in regards to other organs, such as the spinal cord, urinary system, or any other nerve, tissue, or organ that might benefit from such stimulation.

FIG. 1 illustrates one embodiment of an implantable stimulation system 100 that includes a control module 102 (e.g., an implantable pulse generator), one or more electrodes 104, and at least one lead 106 coupling the one or more of electrodes to the control module 102. Electrodes 104 are disposed along the distal end 118 of the lead, while the control module 102 is connected to the lead's proximal end 116. Throughout this disclosure, the term "distal" refers to the end away from the control module, while the term "proximal" refers to the end toward the control module.

One or more components of the stimulation system 100 are typically implanted into a patient's body for a variety of applications including, but not limited to, brain stimulation, neural stimulation, spinal cord stimulation, or muscle stimulation. For example, a portion of the lead 106 and the electrodes 104 may be implanted in the patient's body, at or adjacent a target region, and the control module 102 may be implanted or present outside the patient's body, for example strapped to the patient's arm, wrist, or taped around her chest. Preferably, the entire stimulation system 100 is implanted in the patient's body. The electrodes 104 are implanted at the target area, and the control module 102 may be implanted in any suitable area within the body large enough to accommodate it, such as the abdominal cavity.

The control module 102 typically includes an electronic subassembly 110 and an optional power source 112 disposed in a sealed housing 108. The control module also includes a connector 114 into which the proximal end 116 of the lead 106 can be plugged to make an electrical connection via conductive contacts (not shown) on the control module 102 and terminals (not shown) on the proximal end of the lead 106. Optionally, one or more lead extensions (not shown) can removably connect lead 106 and control module 102 to extend the distance between those elements. For example, when the control module 102 is implanted at a distance from the target area or left outside the patient's body, one or more lead extensions may be utilized.

The control module 102 generates electrical impulses, which are provided to the electrodes 104 through the lead 106. These electrical impulses can, for example, disrupt pain signals transmitted to the brain from the target nerve, muscle, or organ, thereby reducing or eliminating pain sensed by the patient. Depending on the degree of pain and the target location, physicians or operators may regulate or modify the strength, duration, and period between impulses using a remote controller (not shown). The controller may be external to the patient's body, and may communicate with the control module 102 wirelessly.

Generally, the lead 106 is an elongated member having a distal end 118 and a proximal end 116. The proximal end 116 is connected to a lead extension or to the control module 102 through terminals 210 (FIG. 2), and the distal end 118 has the electrodes 104, which may, for example, be provided as paddle electrodes or inline electrodes.

The electrodes 104 may be configured in any arrangement along the distal end of the lead. One configuration used for a percutaneous lead, as depicted in FIG. 1, includes multiple ring electrodes positioned along the distal portion of the elongated lead 106.

In another configuration, the electrodes 104 may be placed on a paddle (not shown), which has an array of electrodes spread out over a flat, paddle-like surface at the distal end 118 of the lead 106. A paddle lead permits the electrode contacts to be spaced apart to provide coverage over a wider stimulation area.

Electrodes 104 can be formed using any conductive, biocompatible material. Examples of suitable material include metals, alloys, conductive polymers, and conductive carbon. The number of electrodes in the electrode array may vary depending on, for example, the target area, and the condition being treated. For example, there may be two, four, six, eight, ten, twelve, fourteen, sixteen, or more electrode. As will be recognized, other numbers of electrodes may also be used.

Electrodes 104 provide electrical current pulses to stimulate nerve fibers, muscle fibers, or other body tissues. In one embodiment, a processor, within the control module 102, is included to control the activation, timing and electrical characteristics of the electrical pulses produced by the electrical stimulation system. For example, the processor can, if desired, control one or more of the timing, frequency, strength, duration, and waveform of the pulses. In addition, the processor can selectively activate the electrodes for use in stimulation.

Figure 2:
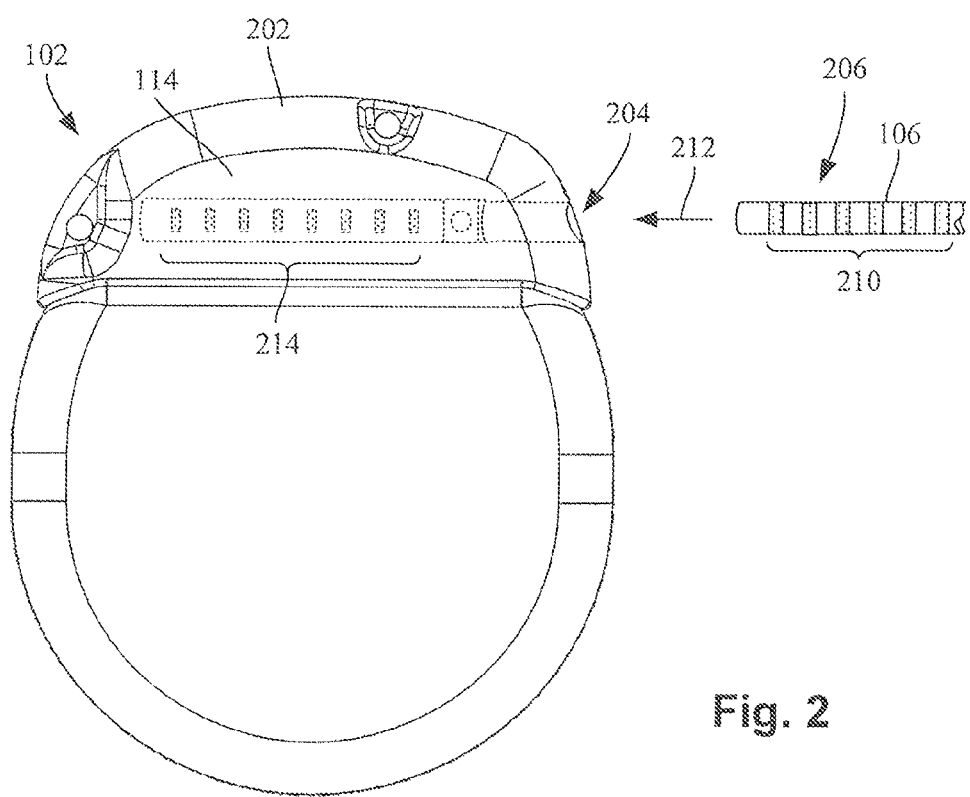
FIG. 2 is a schematic side view of one embodiment of a proximal portion of a lead and a control module of an electrical stimulation system, according to the invention.

FIG. 2 illustrates the proximal end of the stimulation system 100. As shown, terminals 210 are disposed at the proximal end 206 of the lead 106 for connection to corresponding connector conductive contacts 214 on control module 102. Conductors 302 (FIGS. 3A-3B) extend from the terminals 210 to the electrodes 104. Typically, one or more electrodes 104 are electrically coupled to each of the terminals 210. In some embodiments, each of the terminals 210 is only connected to one electrode 104. The conductors may be embedded in the non-conductive material of the lead 106, or the conductors may be disposed in one or more lumens (not shown) extending along the lead 106. In some embodiments, there is an individual lumen for each conductor. In other embodiments, two or more conductors may extend through a single one of the lumens.

In FIG. 2, the proximal end of the lead 106 is adapted and arranged for insertion into the control module 102. The connector 114 defines at least one port 204 into which the proximal end 206 of lead 106 with terminals 210 can be inserted, as shown by directional arrow 212. Each port 204 includes multiple conductive connector contacts 214. When lead 106 is inserted into the port 204, the conductive contacts 214 can be aligned with terminals 210 to electrically couple control module 102 to electrodes 104. To this end, the terminals 210 and conductive contacts 214 are designed so that each of the terminals 210 aligns with a corresponding contact on the connector.

Figure 3A:
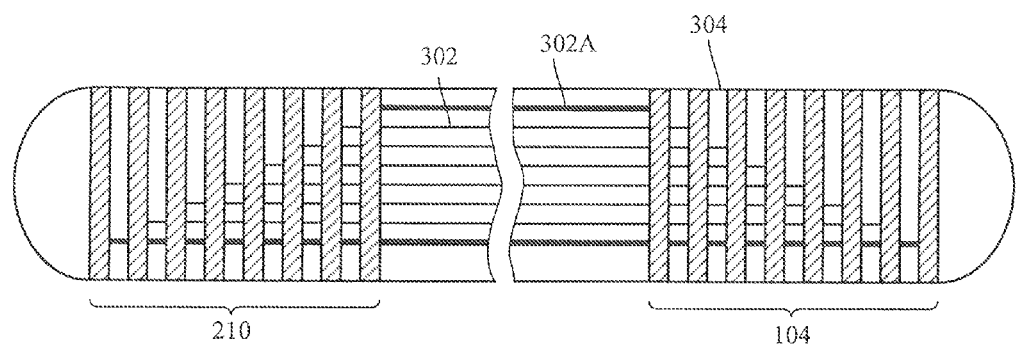
FIGS. 3A and 3B are schematic views of different embodiments of a lead, according to the invention.
Figure 3B:
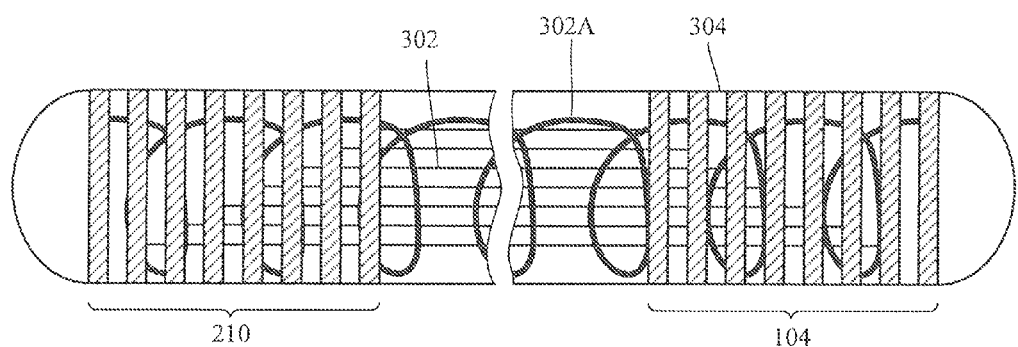

FIGS. 3A and 3B illustrate a schematic view of the lead 106. As shown, lead 106 includes electrodes 104 disposed at the distal end 118 and terminals 210 at its proximal end 116. As previously discussed, each electrode 104 is connected to a corresponding terminal 210 using a conductor 302 which may be, for example, a single or multi-filar wire. The illustrated embodiment shows eight electrodes 104 connected to corresponding eight terminals 210 by conductors 302. It should be understood that the number of electrodes, terminals, and conductors may vary, as desired.

It has been found that a lead with multiple conductors may have uneven RF current induction between the conductors when placed in an RF field, such as the field generated during a MRI procedure. When the induced current is dissipated into the adjoining tissues through the electrodes, the unevenness of the current may result in excessive or damaging tissue heating at certain electrodes. For example, in at least some instances, more heating occurs at tissue adjoining the first or last electrodes, or both, in a linear electrode array such as that illustrated in FIG. 3A. It will be understood, however, that it is possible that more heating might be associated with any particular electrode in an array depending on a variety of design factors. In at least some instances, it is desirable to alter this arrangement of induced current to more evenly distribute the heating of tissue around the array of electrodes. This may prevent or reduce damage to particular regions of tissue. Uneven current distribution may result in "hot spots" where tissue damage may occur or be worse. Similarly, uneven current distribution may also cause damage to system electronics, such as electronics in the control module. A more even distribution of the induced current among the conductors of the lead may also alleviate the damage.

The RF impedance of the individual conductors 302 can be made different from one another to provide more uniform RF energy distribution to the electrodes 104 or terminals 210, or more uniform heating of tissue adjacent the electrodes, or any combination thereof. In at least some embodiments, the magnitude of the RF impedance of at least one conductor is at least 25%, 40%, 50%, 75%, 100%, 125%, 150%, 200%, or more than at least one of the other conductors. In at least some embodiments, the real part or the imaginary part (or both parts) of the RF impedance of at least one conductor is at least 25%, 40%, 50%, 75%, 100%, 125%, 150%, 200%, or more than at least one of the other conductors. In some embodiments, only one or two conductors have a RF impedance different from the other conductors (and optionally different from each other). In other embodiments, more than two (e.g., three, four, five, six, eight, or more) conductors can have RF impedances different from the other conductors. In some embodiments, each conductor has a RF impedance that differs in magnitude (or in the real part or in the imaginary part) by at least 25%, 40%, 50%, 75%, 100%, 125%, 150%, 200%, or more from every other conductor. The RF impedance may be determined for a particular frequency, such as an MRI frequency (e.g., 64 MHz, 128 MHz, or 256 MHz), or over a range of frequencies.

The configuration or materials of one or more conductors can be different from the other conductors to vary the RF impedance of the conductors. For example, a difference in the diameter or length of one or more conductors can produce a difference in the RF impedance. In at least some embodiments, one conductor is at least 10%, 15%, 25%, 50%, 75%, 100%, 125%, 150%, 200% or more longer than at least one of the other conductors. Alternatively, the material of one or more conductors, or the insulator around the conductor(s), can be different from the other conductors.

In FIG. 3A, one or conductors 302 are modified to provide conductor(s) with higher RF impedance 302A. In some embodiments, the diameter of one or more of the conductors is smaller than the diameter of other conductors to provide higher RF impedance. In at least some embodiments, one conductor has a diameter that is at least 10%, 15%, 25%, 40%, 50%, or more smaller than the diameter of at least one of the other conductors. It will be understood that the diameter of a multi-filar wire can also be altered by altering the number of filar or the diameter of individual filar.

As an example, the diameter of the conductors 302 connecting the distal-most electrode to the distal-most terminal and proximal-most electrode to the proximal-most terminal (illustrated as darker lines in FIG. 3A) is smaller to provide higher RF impedance. Although the illustrated embodiment depicts the first and eighth conductors as higher RF impedance conductors 302A, it should be understood that any conductor may be modified as a higher (or lower) RF impedance conductor.

As shown in FIG. 3B, a conductor 302A may also be differently oriented in relation to the other conductors 302. For example, the length of a particular conductor may be extended by coiling all, or a portion, of the conductor 302A to modify its RF impedance.

Figure 4:
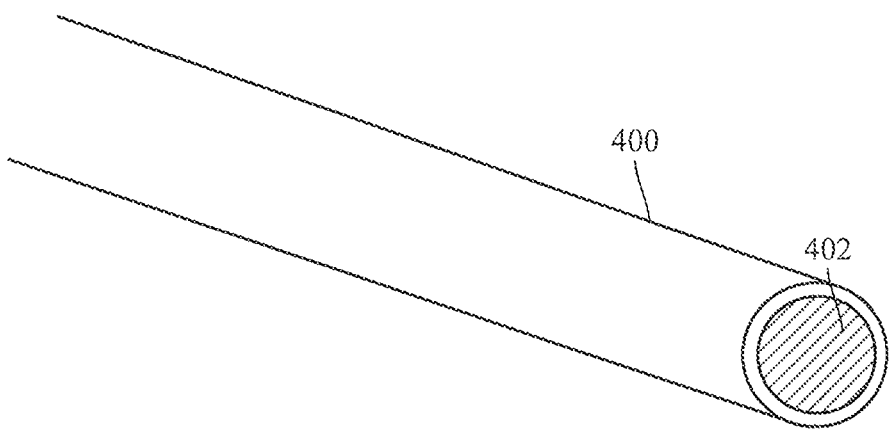
FIG. 4 is a schematic perspective/cross-sectional view one embodiment of a conductor, according to the invention.

In at least some embodiments, the RF impedance of conductor 302 may be made different from other conductors by using a different insulating material (or a different thickness of the insulating material) around the conductor. The selected insulating material can alter the capacitive coupling of the RF field into the conductor or cross-coupling between the conductor and other conductors. This may be manifested, for example, as a difference in the complex impedance of one conductor relative to other conductors. As shown in FIG. 4, the insulating material 400 is disposed around a conductor 402. The insulating material is typically a polymer or other viscoelastic materials, such as, for example, ethylene tetrafluoroethylene (ETFE) or perfluoroalkoxy (PFA).

Figure 5:
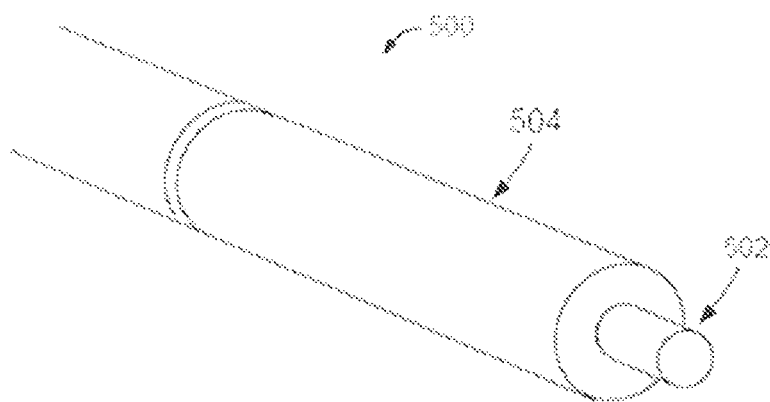
FIG. 5 is a schematic perspective/cross-sectional view of one embodiment of a conductor, according to the invention.

In at least some embodiments, the RF impedance of a conductor 302 may be different by using a different composition of the conductor. As an example, a conductor can be made using one or more filars, each filar having a drawn filled tube (DFT) construction as illustrated in FIG. 5. The conductor 500 of FIG. 5 has an inner core 502 and an outer layer 504. Both the inner core and outer layer are conductive, but are made of different materials Exemplary metals and alloys used for the core 502 and the outer layer 504 include, for example, platinum, silver, MP35N alloy, or any other suitable biocompatible conducting material. As an example, a DFT construction may include a silver or platinum core with an outer layer of MP35N alloy. It is found that such a construction with a platinum core has a RF impedance about six times higher than the RF impedance of a similar construction with a silver core. It will be recognized that altering the diameters of the core or outer layer or both will also alter RF impedance. It will be further recognized that each filar in a multi-filar wire could have a core and an outer layer and that the core and outer layer of each filar may be the same or different from the other filars.

It will be recognized that the various embodiments described above for altering RF impedance of a conductor can be combined in any manner. For example, the diameter of a conductor, as well as the composition of the conductor or the insulating material around the conductor (or both), can be different from other conductors. This will result in conductors of with different RF impedance characteristics. It will also be recognized that the use of different materials in the conductor or insulating material composition may be applied to one or more portions of the conductor or to the entire conductor. It will also be recognized that the RF impedance of a conductor can be made different by using circuit elements such as, for example, resistors, capacitors, inductors, or the like or any combination thereof which are coupled to the conductor.

The conductors in the lead can be straight, coiled, or any combination thereof. For example, U.S. Pat. Nos. 8,335,570; 8,364,279; and 8,380,324; U.S. Patent Application Publication Nos. 2008/0243218; 20080262584; 2010/0256693; 2011/0046706; and 2012/0158072, all of which are incorporated by reference, describe conductors that include straight and coiled sections.

The leads and stimulation systems described herein may be used in any suitable therapy and medical or non-medical procedure, including any medical procedure where one or more body parts are provided electrical stimulation. Apart from spinal cord stimulation or deep brain stimulation, it may be applicable to peripheral nerve stimulation, cardiac stimulation, or any other neuromodulation application involving the use of leads. The leads and stimulation systems can be used in any device seeking MRI compatibility including, but not limited to, neurostimulators, cardiac stimulators, and cochlear implants.

While the present disclosure has been described by means of specific embodiments and applications thereof, numerous modifications and variations could be made thereto by those skilled in the art without departing from the scope of the present disclosure set forth in the claims.

What is claimed is:

1. An implantable stimulation lead, comprising:
a lead body having a proximal end and a distal end;
a plurality of electrodes disposed along the distal end of the lead body;
a plurality of terminals disposed along the proximal end of the lead body, and
a plurality of conductors disposed in the lead body and comprising a first conductor and a second conductor, each conductor electrically coupling at least one of the electrodes to at least one of the terminals, wherein, at 65 MHz, the first conductor has a RF impedance comprising an imaginary part that is at least 25% greater in magnitude than an imaginary part of a RF impedance of the second conductor, wherein at least a portion of the first conductor is coiled and the second conductor is straight.

2. The implantable stimulation lead of claim 1, wherein the first conductor has a different material composition from the second conductor.

3. The implantable stimulation lead of claim 2, wherein the first conductor and the second conductor each comprise an inner core and an outer layer disposed around the inner core, wherein a composition of at least one of the inner core or outer layer differs between the first conductor and the second conductor.

4. The implantable stimulation lead of claim 3, wherein the outer layers of the first and second conductors have a same composition and the inner cores of the first and second conductors have different compositions.

5. The implantable stimulation lead of claim 1, wherein, at 65 MHz, the imaginary part of the RF impedance of the first conductor is at least 50% greater in magnitude than the imaginary part of the RF impedance of the second conductor.

6. The implantable stimulation lead of claim 1, wherein, at 65 MHz, the imaginary part of the RF impedance of the first conductor is at least 100% greater in magnitude than the imaginary part of the RF impedance of the second conductor.

7. The implantable stimulation lead of claim 1, wherein the first conductor has a diameter that is at least 10% smaller than a diameter of the second conductor.

8. The implantable stimulation lead of claim 7, wherein the first conductor has a different material composition from the second conductor.

9. The implantable stimulation lead of claim 1, wherein the first conductor has a diameter that is at least 15% smaller than a diameter of the second conductor.

10. The implantable stimulation lead of claim 1, wherein the first conductor has a diameter that is at least 25% smaller than a diameter of the second conductor.

11. The implantable stimulation lead of claim 1, wherein the first conductor and the second conductor each having a different insulating material disposed around the conductor.

12. The implantable stimulation lead of claim 1, wherein the first conductor is a multi-filar conductor.

13. The implantable stimulation lead of claim 1, wherein a length of the first conductor is at least 10% greater than a length of the second conductor.

14. The implantable stimulation lead of claim 1, wherein a length of the first conductor is at least 25% greater than a length of the second conductor.

15. An implantable stimulation system comprising:
   a control module for producing electrical pulses; and
   the implantable stimulation lead of claim 1 coupleable to the control module.

16. A method for tissue stimulation, the method comprising:
   implanting the implantable stimulation lead of claim 1 within a body; and
   providing electrical stimulation signals to the electrodes of the implantable stimulation lead to stimulate adjacent tissue.

17. The method of claim 16, further comprising coupling the implantable stimulation lead to a control module.

18. The method of claim 17, further comprising implanting the control module.

19. The method of claim 16, further comprising exposing the implanted stimulation lead to a RF field generated during an MRI procedure.

* * * * *